United States Patent
Nikolaus (10) Patent No.: US 7,719,290 B2
(45) Date of Patent: May 18, 2010

(54) CIRCUIT CONFIGURATION AND METHOD FOR MEASURING HUMIDITY

(75) Inventor: Gerhard Nikolaus, Engerwitzdorf (AT)

(73) Assignee: E+E Elektronik Ges.m.b.H., Engerwitzdorf (AT)

( * ) Notice: Subject to any disclaimer, the term of this patent is extended or adjusted under 35 U.S.C. 154(b) by 151 days.

(21) Appl. No.: 11/888,200

(22) Filed: Jul. 30, 2007

(65) Prior Publication Data

US 2008/0024110 A1 Jan. 31, 2008

(30) Foreign Application Priority Data

Jul. 28, 2006 (DE) .................. 10 2006 034 931

(51) Int. Cl.
- G01R 27/26 (2006.01)
- G01R 27/08 (2006.01)
- G01N 27/22 (2006.01)

(52) U.S. Cl. .................. 324/667; 324/694; 73/335.04

(58) Field of Classification Search .................. 324/667, 324/694

See application file for complete search history.

(56) References Cited

U.S. PATENT DOCUMENTS

| | | | |
|---|---|---|---|
| 4,426,616 | A | 1/1984 | Maier |
| 5,303,164 | A * | 4/1994 | Masson et al. ............. 702/65 |
| 5,418,466 | A | 5/1995 | Watson et al. |
| 5,483,172 | A | 1/1996 | Radford |
| 5,844,138 | A | 12/1998 | Cota |
| 6,433,560 | B1 * | 8/2002 | Hansen et al. ............. 324/668 |
| 6,437,582 | B1 * | 8/2002 | Rode et al. ............. 324/664 |
| 7,030,630 | B2 | 4/2006 | Haas et al. |
| 2005/0231360 | A1 * | 10/2005 | Fujimori et al. ............. 340/539.23 |

FOREIGN PATENT DOCUMENTS

| | | |
|---|---|---|
| EP | 1 411 349 | 12/2005 |
| GB | 2 344 422 | 6/2000 |

OTHER PUBLICATIONS

H.-R. Tränkler and E. Obermeier, "Sensortechnik," *Handbuch für Praxis and Wissenschaft*,( "Sensor Technology", *Handbook for Practice and Science*. : pp. 1247-1250, (1998).
H. Lemme, "Sensoren in der Praxis," *Elecronik*, ("Sensors in Practice"), pp. 327-336, (1993).
Search Report, European Patent Application No. 07 00 8614, dated Nov. 27, 2007 (translated).

* cited by examiner

*Primary Examiner*—Jeff Natalini
(74) *Attorney, Agent, or Firm*—Kenyon & Kenyon LLP (57) ABSTRACT

A circuit configuration for measuring air humidity includes a measuring system which includes an oscillator unit and a signal-processing unit, as well as a frequency-determining impedance, which is determined largely by a parallel connection of a capacitive humidity sensor and a parasitic resistance. The frequency-determining impedance is connected to the oscillator unit, which includes an oscillator having an oscillation frequency that is a function of the frequency-determining impedance. The oscillator unit includes a switchable impedance, which can be connected in addition to the frequency-determining impedance, the oscillator thereby being switchable from a first frequency range to a second frequency range. An oscillator signal having the oscillation frequency of the oscillator is supplied to the signal-processing unit in which the frequency of the oscillator signal is able to be measured, and a correction value to compensate for the influence of the parasitic parallel resistance on the oscillation frequency of the oscillator is ascertainable as a function of the difference between a first measurement of the frequency of the oscillator signal in the first frequency range and a second measurement of the frequency of the oscillator signal in the second frequency range.

16 Claims, 4 Drawing Sheets

CIRCUIT CONFIGURATION AND METHOD FOR MEASURING HUMIDITY

CROSS-REFERENCE TO RELATED APPLICATIONS

The present application claims priority to Application No. 10 2006 034 931.8, filed in the Federal Republic of Germany on Jul. 28, 2006, which is expressly incorporated herein in its entirety by reference thereto.

FIELD OF THE INVENTION

The present invention relates to a circuit configuration for measuring the air humidity and to a method for measuring the air humidity using such a circuit configuration.

BACKGROUND INFORMATION

Capacitive humidity sensors are mainly used for measuring the air humidity, such as, for example, in air-conditioning technology for controlling an interior environment. Generally, they are thin-film sensors whose measured quantity is the moisture-dependent capacitance of the polymer layer between the electrodes. Sensors of this type are described, for example, in H.-R. Traenkler, E. Obermeier, "Sensortechnik, Handbuch fuer Praxis und Wissenschaft" ("Sensor Technology, Handbook for Practice and Science"), Springer Verlag, 1998, pages 1247 to 1250.

In order to be able to measure the capacitance of the sensor, oscillator circuits are often used in which the capacitive sensor is the frequency-determining member. In this case, a value for the air humidity may be ascertained simply by measuring the oscillator frequency and assigning a humidity value to the result of the measurement. Examples for such circuits in the field of moisture measurement can be found, for example, in H. Lemme, "Sensoren in der Praxis" ("Sensors in Practice"), Franzis-Verlag, 1993, pages 327 to 336.

U.S. Pat. No. 5,844,138 describes a device for measuring humidity, in which a capacitive humidity sensor is the frequency-determining element of an oscillator. The instantaneous air humidity is ascertained by measuring the oscillator frequency and converting it into a humidity value with the aid of calibration data stored in a memory unit.

Particularly in an industrial environment, parasitic parallel resistances, caused by contamination of the sensor connections or by material properties of the sensor itself, appear at the capacitive humidity sensor and also influence the oscillator frequency of the measuring circuit, and thereby falsify the measurement result. Such changes of the impedance connected to the oscillator are not described as being taken into account in U.S. Pat. No. 5,844,138.

The measuring error which comes about due to the parallel connection of a parasitic resistance to the capacitive humidity sensor can be corrected if not only the capacitance, but also the impedance of the measuring sensor is measured, since phase information is also acquired at the same time, and the error produced by the parasitic parallel resistance can be eliminated. However, circuit configurations for measuring impedance are quite complicated and cost-intensive.

European Published Patent Application No. 1 411 349 describes a method for recording the air humidity, in which the charging duration and/or discharging duration of a capacitive humidity sensor is recorded via two different measuring resistors, and the capacitance of the sensor is calculated from the results. In this case, the capacitive sensor is modeled by a parallel connection of an ideal capacitor with an ohmic resistance, both the resistance value and the capacitor value being a function of the moisture and the temperature.

SUMMARY

Example embodiments of the present invention provide a circuit configuration for measuring the air humidity having a capacitive humidity sensor, by which it is possible to easily compensate for parasitic changes in the impedance of the humidity sensor.

Example embodiments of the present invention provide a method for measuring the air humidity using a circuit configuration, by which it is possible to easily compensate for parasitic changes in the impedance of the humidity sensors.

According to an example embodiment of the present invention, a circuit configuration is provided, having a measuring system which includes an oscillator unit and a signal-processing unit, as well as a frequency-determining impedance that is determined largely by a parallel connection of a capacitive humidity sensor and a parasitic resistance. The frequency-determining impedance is connected to the oscillator unit which includes an oscillator having an oscillation frequency that is a function of the frequency-determining impedance. The oscillator unit includes a switchable impedance which is able to be connected additionally to the frequency-determining impedance, the oscillator thereby being switchable from a first frequency range to a second frequency range. An oscillator signal having the oscillation frequency of the oscillator is supplied to the signal-processing unit, in which the frequency of the oscillator signal is able to be measured, and a correction value to compensate for the influence of the parasitic parallel resistance on the oscillation frequency of the oscillator is ascertainable as a function of the difference between a first measurement of the frequency of the oscillator signal in the first frequency range and a second measurement of the frequency of the oscillator signal in the second frequency range.

The switchable impedance may be switched in by a parallel connection of a reference capacitor to the frequency-determining impedance, since the influence of the parasitic resistance on the oscillation frequency of the oscillator increases, with the result that the difference between the first measurement of the frequency of the oscillator signal in the first frequency range and the second measurement of the frequency of the oscillator signal in the second frequency range enlarges. The accuracy in ascertaining the correction value is thereby increased.

According to an example embodiment of the present invention, a circuit configuration for measuring air humidity includes: a measurement system including an oscillator unit and a signal-processor unit, the oscillator unit including an oscillator and a switchable impedance; and a frequency-determining impedance including a capacitive humidity sensor and a parasitic resistance connected in parallel, the frequency-determining impedance connected to the oscillator unit. An oscillation frequency of the oscillator is a function of the frequency-determining impedance, and the oscillator is switchable from a first frequency range to a second frequency range by connection of the switchable impedance to the frequency-determining impedance. The oscillator unit is configured to supply an oscillator signal having the oscillation frequency of the oscillator to the signal-processor unit, and the signal-processor unit is configured to measure the frequency of the oscillator signal and to ascertain a correction value to compensate for influence of the parasitic resistance on the oscillation frequency as a function of a difference between a first measurement of the frequency of the oscillator signal in the first frequency range and a second measurement of the frequency of the oscillator signal in the second frequency range.

The signal-processor unit may include: a measurement unit configured to measure the frequency of the oscillator signal; a correction-value memory including correction values to compensate for the influence of the parasitic resistance on the frequency of the oscillator signal as a function of the difference between the first measurement of the frequency of the oscillator signal in the first frequency range and the second measurement of the frequency of the oscillator signal in the second frequency range; an evaluation unit configured to process a result of at least one of (a) the first measurement and (b) the second measurement with a correction value from the correction-value memory to form a humidity value; and a control unit configured to control the measurement processes.

The switchable impedance may include a reference capacitor and a switch device, and the oscillator may be switchable to the second frequency range by a parallel connection of the reference capacitor to the frequency-determining impedance by energizing the switch element.

The switch element may be energizable by a control unit of the signal-processor unit via a switch line.

The signal-processor unit may be arranged as at least one of (a) an FPGA, (b) an ASIC and (c) a microcontroller.

According to an example embodiment of the present invention, a circuit configuration for measuring air humidity includes: measuring means including an oscillator unit and signal-processing means, the oscillator unit including oscillating means and switchable impedance means; and frequency-determining impedance means including capacitive humidity sensing means and a parasitic resistance means connected in parallel, the frequency-determining impedance means connected to the oscillator unit. An oscillation frequency of the oscillating means is a function of the frequency-determining impedance means, and the oscillating means is switchable from a first frequency range to a second frequency range by connecting the switchable impedance means to the frequency-determining impedance means. The oscillator unit is for supplying an oscillator signal having the oscillation frequency of the oscillating means to the signal-processing means, and the signal-processing means is for measuring the frequency of the oscillator signal and for ascertaining a correction value to compensate for influence of the parasitic resistance means on the oscillation frequency as a function of a difference between a first measurement of the frequency of the oscillator signal in the first frequency range and a second measurement of the frequency of the oscillator signal in the second frequency range.

According to an example embodiment of the present invention, a method for measuring air humidity includes: performing, in a signal-processor unit, a first measurement of a frequency of an oscillator signal in a first frequency range of an oscillator; switching the oscillator from the first frequency range to a second frequency range by connecting a switchable impedance to a frequency-determining impedance; performing, in the signal-processor unit, a second measurement of the frequency of the oscillator signal in the second frequency range of the oscillator; and ascertaining a correction value to compensate for an influence of a parasitic resistance on the frequency of the oscillator signal as a function of a difference between the first measurement and the second measurement.

The frequency of the oscillator signal may be measured in the signal-processing unit by a measuring unit, and the method may include outputting a result of the measurements to an evaluation unit.

The method may include determining the difference between the first measurement and the second measurement by the evaluation unit, and the evaluation unit may ascertain the correction value in the ascertaining step by fetching the correction value from a correction-value memory as a function of the difference between the first measurement and the second measurement.

The measurements may be controlled by a control unit of the signal-processor unit.

The switchable impedance may include a reference capacitor and a switch device, and the oscillator may be switched in the switching step to the second frequency range by energizing the switch device by the control unit of the signal-processor unit via a switching line.

The energizing of the switch device may connect, in parallel, the reference capacitor and the frequency-determining impedance.

The method may include processing at least one of (a) a result of the first measurement and (b) a result of the second measurement with the ascertained correction value to form a humidity value.

The method may include generating a warning signal if the influence of the parasitic resistance on the frequency of the oscillator signal exceeds a limiting value.

The method may be performed by the circuit configuration as described herein.

According to an example embodiment of the present invention, a method for measuring air humidity includes: performing a first measurement of a frequency of an oscillator signal in a first frequency range of an oscillator; switching the oscillator from the first frequency range to a second frequency range by connecting a switchable impedance to a frequency-determining impedance; performing a second measurement of the frequency of the oscillator signal in the second frequency range of the oscillator; and ascertaining a correction value to compensate for an influence of a parasitic resistance on the frequency of the oscillator signal as a function of a difference between the first measurement and the second measurement.

Example embodiments of the present invention are described in more detail below with reference to the appended Figures.

DETAILED DESCRIPTION

Figure 1:
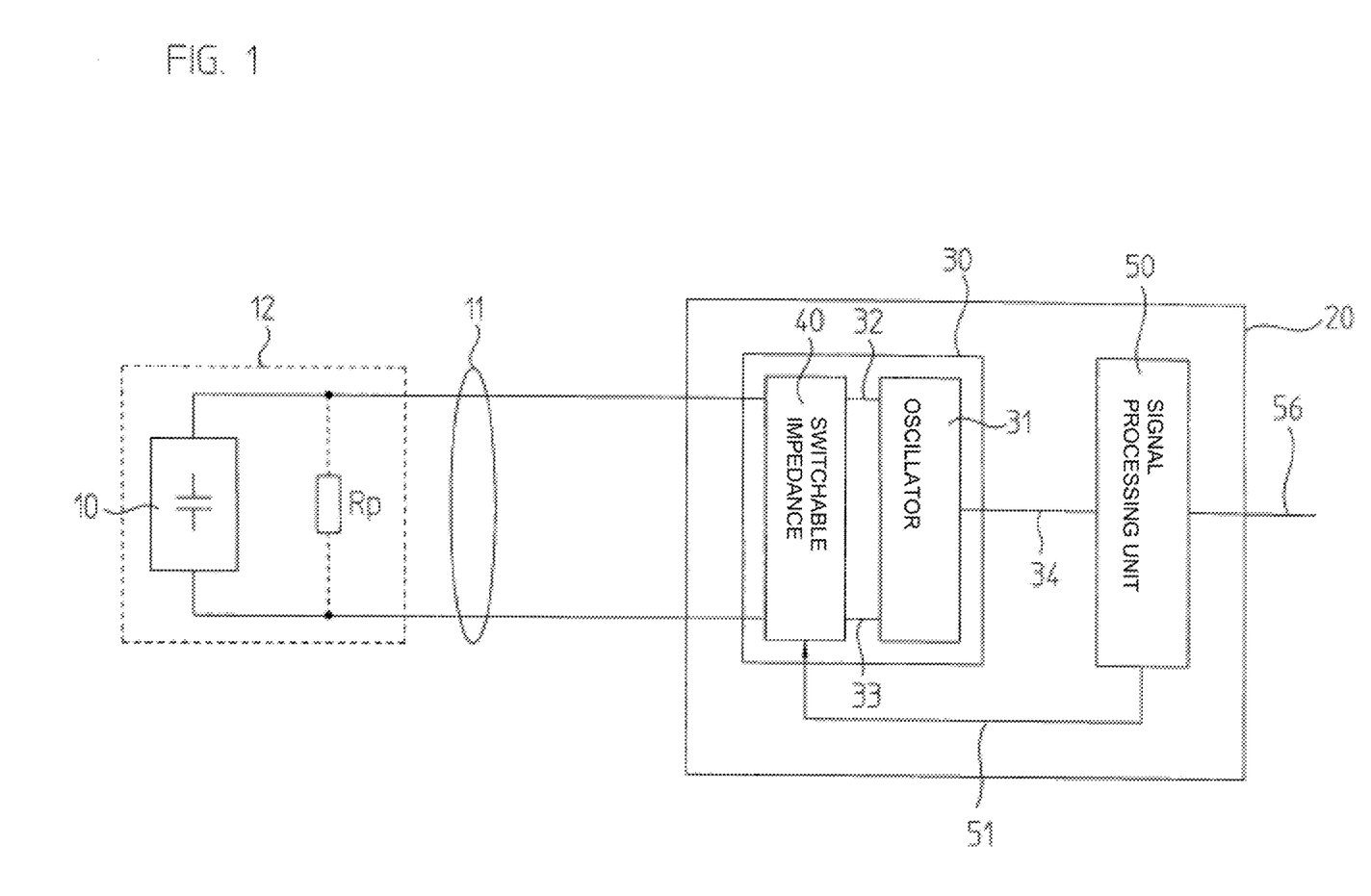
FIG. 1 is a schematic block diagram of a circuit configuration for measuring air humidity according to an example embodiment of the present invention.

FIG. 1 is a schematic block diagram of a device for measuring humidity according to an example embodiment of the present invention. A capacitive humidity sensor 10 is connected via a connecting cable 11 to an oscillator unit 30 in a measuring system 20. Oscillator unit 30 includes a switchable impedance 40 and an oscillator 31. Oscillator 31 is arranged such that its oscillation frequency is determined by the impedance, especially the capacitance, which is connected to inputs 32, 33 of oscillator 31. By additionally connecting the switchable impedance to inputs 32, 33 of oscillator 31, it is switchable from a first frequency range to a second frequency range.

Measuring system 20 further includes a signal-processing unit 50, to which an oscillator signal 34 having the oscillation frequency of oscillator 31 is supplied. Signal-processing unit 50 includes a device to measure the frequency of oscillator signal 34, and to ascertain a humidity value 56 from the result. Humidity value 56 is output by measuring system 20 for further processing, for example, to an air conditioning unit for controlling the interior environment, or to a display unit for the display of humidity value 56.

The oscillation frequency of oscillator 31, aside from the switching status of switchable impedance 40, may be dependent only on the capacitance of capacitive humidity sensor 10, which changes as a function of the air-humidity. That is, by measuring the frequency of oscillator signal 34 in signal-processing unit 50, it is possible to determine the capacitance of capacitive humidity sensor 10, and therefore the instantaneous value of the air humidity.

Parallel to capacitive humidity sensor 10 may be a parasitic resistance $R_p$, which together with capacitive humidity sensor 10, forms a frequency-determining impedance 12 that influences the oscillation frequency of oscillator 31. In principle, parasitic resistance $R_p$ is always present, for instance, in the form of insulation resistances that occur, for example, in connecting cable 11, or between the connections of capacitive humidity sensor 10, or between connecting terminals or plug pins at measuring system 20. In interference-free operation and in the case of an error-free arrangement, parasitic resistance $R_p$ may have such a high ohmic value (e.g., >10 MOhm) that it can be disregarded for many applications. In harsh industrial surroundings, however, it often happens that in the course of time, parasitic resistance $R_p$ becomes low-impedance due to contamination, e.g., by dust deposits between the contacts of capacitive humidity sensor 10, often also in conjunction with moisture, etc., until it noticeably influences the oscillation frequency of oscillator 31 and therefore the measuring result, and leads to measuring errors. In practice, parasitic resistance $R_p$ causes a reduction in the oscillation frequency of oscillator 31, since due to it, the charging current of capacitive humidity sensor 10 decreases or its charging time increases.

Signal-processing unit 50 is able, via switching line 51, to switch oscillator 31 from a first frequency range to a second frequency range by additionally connecting switchable impedance 40 to frequency-determining impedance 12. Since the influence of parasitic resistance $R_p$, thus the decrease in the oscillation frequency of oscillator 31 caused by parasitic resistance $R_p$, takes effect differently in the first frequency range and in the second frequency range, signal-processing unit 50 is able to compensate for it based on the difference between a first measurement of the frequency of oscillator signal 34 in the first frequency range of oscillator 31 and a second measurement of oscillator single 34 in the second frequency range.

Switchable impedance 40 may be largely capacitive, and the switching-in may be accomplished by connecting it in parallel to frequency-determining impedance 12. The total capacitance is thereby increased, resulting in that the total charging time of the capacitances increases, and as a result, the oscillation frequency of oscillator 31 decreases in the second frequency range, and the influence of parasitic resistance $R_p$ has a stronger effect. The result of this is that the difference from the two measurements can be determined with greater accuracy.

Figure 2:
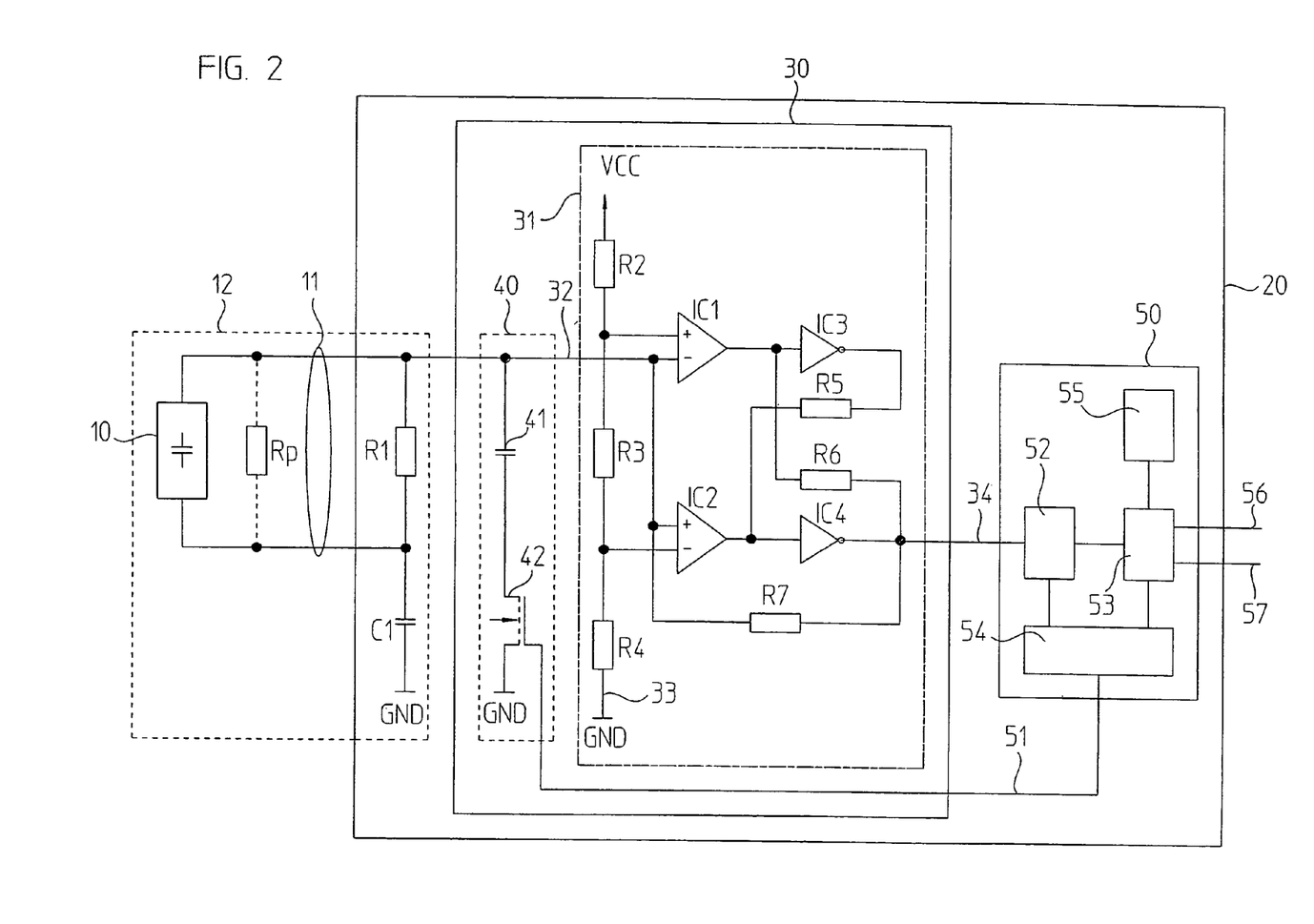
FIG. 2 is a schematic block diagram of a circuit configuration for measuring air humidity according to an example embodiment of the present invention.

FIG. 2 is a schematic circuit diagram of a circuit configuration for measuring air humidity according to an example embodiment of the present invention. Components already described with reference to FIG. 1 have the same reference numerals in FIG. 2.

Capacitive sensor 10 with parallel-connected parasitic resistance $R_p$ is connected via connecting cable 11 to measuring system 20. In so doing, one terminal of capacitive sensor 10 is connected directly to oscillation-active input 32 of oscillator 31. The second terminal of the capacitive sensor is connected via a coupling capacitor C1 to second input 33 of oscillator 31, which in this example is identical to reference point GND of the circuit of oscillator 31. In comparison to capacitive humidity sensor 10, the coupling capacitor has a high capacitance, e.g., more than 100-fold the capacitance value of capacitive humidity sensor 10. The task of this coupling capacitor C1 is to reduce the direct-voltage component at capacitive humidity sensor 10. In order to prevent coupling capacitor C1 from having to charge or discharge via capacitive humidity sensor 10, a charging resistor R1 is additionally provided, which is connected in parallel to capacitive humidity sensor 10. The ohmic value of charging resistor R1 may be high, e.g., in the area of 10 MOhm. Thus, in this example, capacitive humidity sensor 10, parasitic resistance $R_p$, coupling capacitor C1 and charging resistor R1 form frequency-determining impedance 12. However, coupling capacitor C1 and charging resistor R1 may be disregarded, since because of their dimensioning, they have virtually no influence on the oscillation frequency of oscillator 31.

In this example, oscillator 31 in oscillator unit 30 includes resistors R2 to R7, two operational amplifiers IC1, IC2 and two digital inverter components IC3, IC4. Oscillator circuits of this kind, also referred to as astable flip-flops, are conventional, and therefore the circuit used is not further described. As an alternative to the circuit illustrated, an integrated timer component, e.g., the widely prevalent timer 555 (e.g., available under the designation LMC555, NE555, TLC555, depending on the manufacturer) with suitable additional wiring could also be used. Oscillator 31 may be configured so that at an average humidity value, it has a fundamental frequency between, e.g., 10 kHz and 1 MHz, which changes sufficiently significantly over the humidity range to be measured, that is, over the capacitance range of capacitive humidity sensor 10, that a reliable measurement of the air humidity as a function of the capacitance of capacitive humidity sensor 10 is possible. If the capacitance of a capacitive humidity sensor 10 varies in a humidity range to be measured of 0% to 100% RH, e.g., between 390 pF and 540 pF, then a change in the oscillator frequency from approximately 55 kHz at 0% air humidity to approximately 40 kHz at 100% air humidity may be viewed as particularly suitable.

Switchable impedance 40 includes a reference capacitor 41, which is able to be switched via a switching element 42 between oscillation-active input 32 and reference point GND of oscillator 31. Switching element 42 is actuated by signal-processing unit 50 via switching line 51. The energizing of switching element 42 brings about a parallel connection of reference capacitor 41 to frequency-determining impedance 12, in particular with capacitive humidity sensor 10. As a result, the oscillation frequency of oscillator 31 drops.

A MOSFET is used as switching element 42. The current which is used to energize the MOSFET is negligibly small. In other arrangements, for instance, when a potential-free contact is required for switching element 42, a relay, for example, may be used as switching element 42.

Oscillator signal 34 is supplied to a measuring unit 52 in signal-processing unit 50, by which the frequency of oscillator signal 34 is able to be measured. Instead of the frequency, the period duration of oscillator signal 34 may also be measured. The result of the measurement is output to an evaluation unit 53, which from the frequency values, ascertains and outputs humidity values 56. To that end, evaluation unit 53 is connected to a correction-value memory 55 which, as a function of the difference of measured values in the first frequency range and in the second frequency range of oscillator 31, stores correction values which are capable of compensating for the influence of parasitic resistance $R_p$ on the oscillation frequency of oscillator 31.

The measuring operation is controlled by a control unit 54 which, via switching line 51, determines the frequency range of oscillator unit 30 and initiates the measurement and evaluation of oscillator signal 34.

For example, when producing the circuit configuration, the correction values may be ascertained in a calibration operation in the case of an ideal setup, in which parasitic resistance $R_p$ is simulated by known resistance values, and its influence on the oscillation frequency of oscillator 31 in the two frequency ranges is recorded. Moreover, if the air humidity is also varied during the calibration operation, humidity values 56 may be assigned directly to the measured oscillator frequencies. For example, correction values may be generated which, in addition to the compensation of the influence of parasitic resistance $R_p$, already contain conversion factors for converting the measured frequency values or period-duration values into humidity values 56.

Since signal-processing unit 50 is a purely digital circuit, it is particularly suitable to be integrated into a complex digital component such as, for example, an FPGA (field programmable gate array) or an ASIC (application specific integrated circuit). A microcontroller may be provided as signal-processing unit 50.

It is further possible to integrate oscillator 31 and signal-processing unit 50 together in one application-specific component or to provide them by a microcontroller.

Figure 3:
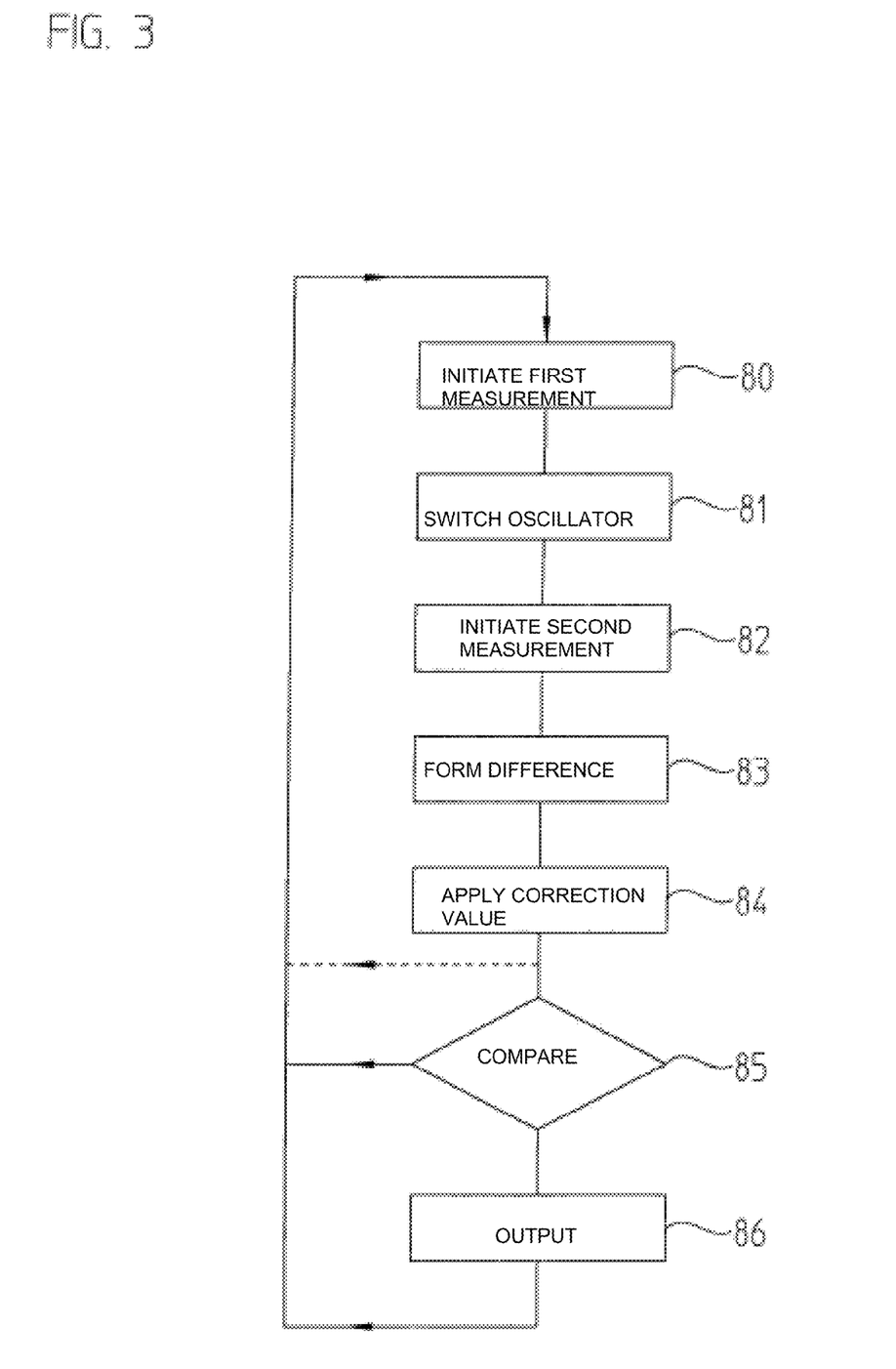
FIG. 3 is a flowchart of a method for measuring air humidity according to an example embodiment of the present invention.

A method for measuring the air humidity is described with reference to the flowchart illustrated in FIG. 3.

In step 80, control unit 54 initiates a measurement of the frequency of oscillator signal 34 in the first frequency range of oscillator 31 by measuring unit 52. The result of the measurement is passed on to evaluation unit 53.

In step 81, control unit 54, via switching line 51, switches oscillator 31 to the second frequency range of oscillator 31 by additionally connecting switchable impedance 40 to capacitive humidity sensor 10. In the example illustrated in FIG. 2, this is achieved by the parallel connection of reference capacitor 41 to frequency-determining impedance 12, using switching element 42.

In step 82, control unit 54 initiates a second measurement of the frequency of oscillator signal 34 in the second frequency range of oscillator 31 by measuring unit 52. The second result is also output to evaluation unit 53.

In step 83, evaluation unit 53 forms the difference from the two measured values and, as a function of the result, fetches from correction-value memory 55 a correction value which is able to compensate for the influence of parasitic resistance $R_p$ on the frequency of oscillator signal 34. Depending upon how correction-value memory 55 is provided, the correction value may be a table value, for example, or one or more coefficients for a mathematical formula. As described above, the correction value may already include a conversion factor for ascertaining a humidity value 56 from the frequency of oscillator signal 34. It should be appreciated that both the result of the first measurement of the frequency of oscillator signal 34, as well as the result of the second measurement of the frequency of oscillator signal 34 are suitable for ascertaining humidity value 56.

In step 84, evaluation unit 53 applies the ascertained correction value to the result of the first measurement of oscillator signal 34 or to the result of the second measurement of oscillator signal 34, and ascertains a corresponding humidity value 56 as a function of the corrected measured value.

As described above, parasitic resistance $R_p$ arises, e.g., due to the effects of contamination which occur during operation of the circuit configuration for measuring the air humidity in a harsh industrial environment. In this context, the value of parasitic resistance $R_p$ drops over the course of time until it finally influences the measuring result. It may happen that with time, the value of parasitic resistance $R_p$ becomes so low-impedance that its influence on the measuring result is no longer able to be offset, or until the oscillator no longer functions. In order to prevent such a failure of the circuit configuration, in a step 85, evaluation unit 53 compares the difference from the two measured values, ascertained in step 83, with a limiting value that corresponds to a minimal value of parasitic resistance $R_p$ that is only just tolerable, and if the minimal value is not attained, in step 86 outputs a warning signal 57 which indicates that a failure of the circuit configuration is immediately imminent. This signal may be used to perform a preventive maintenance of the circuit configuration, for example, by cleaning the connection contacts or by replacement of capacitive humidity sensor 10.

Generally, the change of parasitic resistance $R_p$ is a slow process. Therefore, it may be provided that a measurement of the frequency of oscillator signal 34 both in the first and in the second frequency range of oscillator 31 is not performed upon each measurement of a humidity value 56, but rather a correction value ascertained one time is used for a specific period of time to compensate for parasitic resistance $R_p$. In particular, the number of switching operations of switching element 42 is thereby reduced. If it is implemented in the form of a mechanical contact, e.g., as a relay contact, the service life may thereby be increased.

Figure 4:
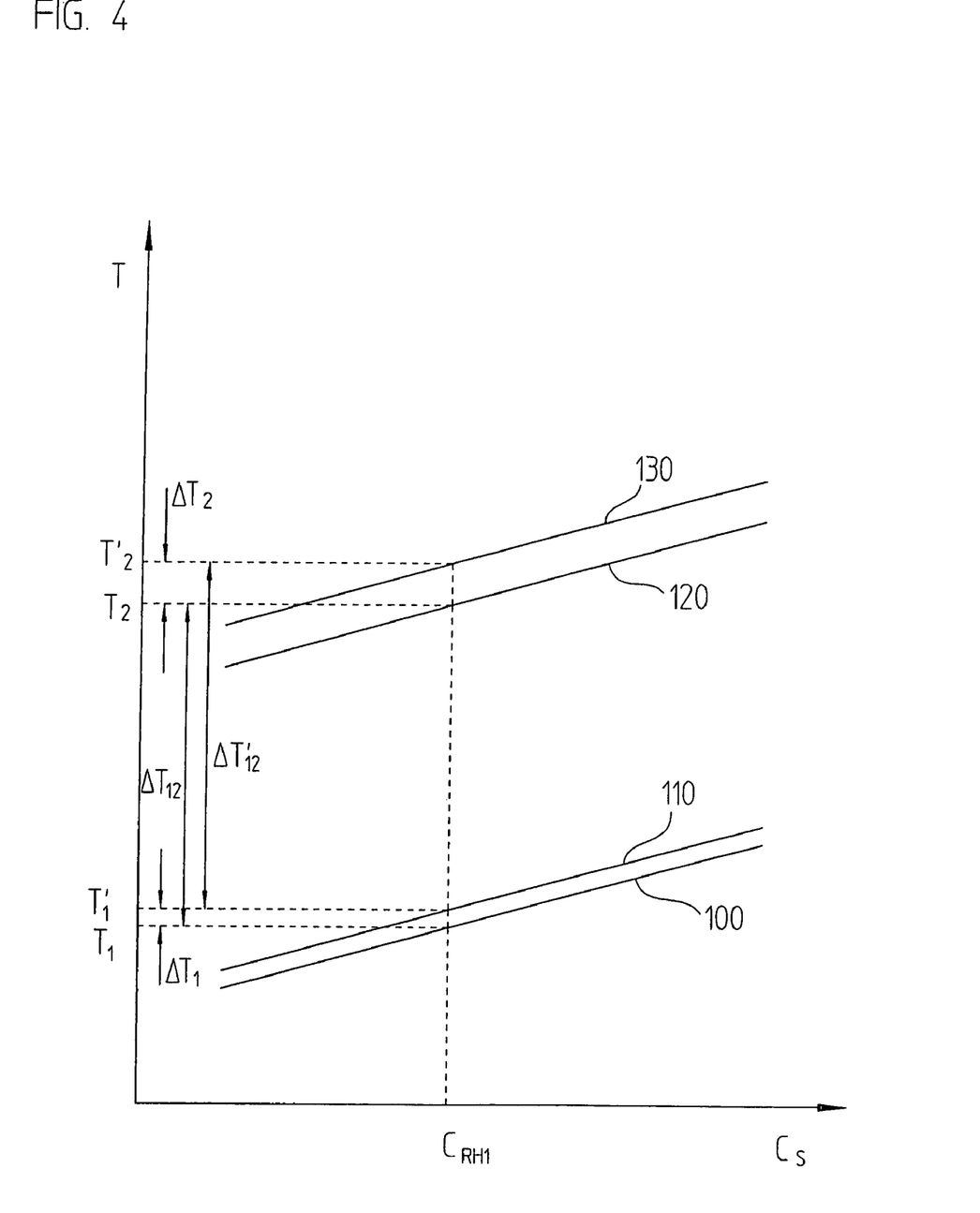
FIG. 4 shows characteristic curves for illustrating the influence of a parasitic resistance on the period duration of the oscillator signal of a circuit configuration such as that illustrated in FIG. 2.

FIG. 4 shows, by way of example, the characteristic of period duration T of oscillator signal 34 as a function of capacitance $C_s$ of capacitive humidity sensor 10, parasitic resistance $R_p$ and the switching status of switchable impedance 40. Based on the known relationship, that period duration T may be converted into a frequency by forming the inverse value, the following observations are also applicable to the frequency of oscillator signal 34, and therefore to the exemplary embodiments described above.

A first characteristic curve 100 shows the characteristic of period duration T in the case of an ideal arrangement, thus without, or very high-ohmic parasitic resistance $R_p$ and in the first frequency range of oscillator 31. A second characteristic curve 110 illustrates how first characteristic curve 100 is shifted in the direction of longer period durations T by the influence of parasitic resistance $R_p$.

A third characteristic curve 120 shows the characteristic of period duration T in the case of an ideal arrangement, this time, however, in the second frequency range, thus with switchable impedance 40 additionally connected. In this instance, the switching-in is provided in accordance with the example embodiment illustrated in FIG. 2 by the parallel connection of a reference capacitor 41 to frequency-determining impedance 12. Since, in this manner, the capacitances of reference capacitor 41 and of capacitive humidity sensor 10 are accumulated, and a longer charging time of the capacitances thereby results, third characteristic curve 120 is shifted up, thus in the direction of greater period durations T, compared to first characteristic curve 100. The influence of parasitic resistance $R_p$ on third characteristic curve 120 is apparent from a fourth characteristic curve 130. It is assumed that parasitic resistance $R_p$ has the same value which also brings about the shift from first characteristic curve 100 to second characteristic curve 110. However, the result of the addition of the capacitances is that parasitic resistance $R_p$ has a stronger effect.

This effect is illustrated once again in FIG. 4 by way of example in the case of an arbitrary value $C_{RH1}$ of capacitive humidity sensor 10. A measurement of period duration T in the first frequency range of oscillator 31 without the influence of parasitic resistance $R_p$ yields a value $T_1$. Parasitic resistance $R_p$ leads to an increase of period duration T of oscillator 31 to the value $T_1'$. A measuring error $\Delta T_1$ results. On the other hand, in the second frequency range of oscillator 31, a shift of period duration T from a value $T_2$ to a value $T_2'$ results due to the influence of parasitic resistance $R_p$, which leads to a measuring error $\Delta T_2$.

Looked at differently, given an ideal arrangement, a switchover from the first frequency range to the second frequency range of oscillator 31 leads to a change of period duration T by an ideal value $\Delta T_{12}$, which changes to a faulty value $\Delta T_{12}'$ as a function of parasitic resistance $R_p$.

On the basis of this relationship, it is possible to ascertain correction values as a function of faulty value $\Delta T_{12}'$, or the difference between faulty value $\Delta T_{12}'$ and ideal value $\Delta T_{12}$, with which the influence of parasitic resistance $R_p$ may be offset.

It should be understood that the circuit configuration hereof and the method hereof are not limited to capacitive humidity sensors, but may also be used with capacitive sensors for measuring other physical quantities, such as capacitive pressure sensors.

What is claimed is:

1. A circuit configuration for measuring air humidity, comprising:
   a measurement system including an oscillator unit and a signal-processor unit, the oscillator unit including an oscillator and a switchable impedance; and
   a frequency-determining impedance including a capacitive humidity sensor and a parasitic resistance connected in parallel, the frequency-determining impedance connected to the oscillator unit;
   wherein an oscillation frequency of the oscillator is a function of (a) the frequency-determining impedance and (b) a falsifying influence of the parasitic resistance, the oscillator switchable from a first frequency range to a second frequency range by connection of the switchable impedance to the frequency-determining impedance;
   wherein the oscillator unit is configured to supply an oscillator signal having the oscillation frequency of the oscillator to the signal-processor unit, the signal-processor unit configured to measure the frequency of the oscillator signal and to ascertain a correction value to compensate for influence of the parasitic resistance on the oscillation frequency as a function of a difference between a first measurement of the frequency of the oscillator signal in the first frequency range and a second measurement of the frequency of the oscillator signal in the second frequency range;
   wherein the influence of the parasitic resistance on the oscillation frequency of the oscillator is different in the first frequency range and the second frequency range; and
   wherein the signal-processor unit is adapted to determine a corrected frequency of the oscillator signal and to ascertain a corrected humidity value from the corrected frequency of the oscillator signal that does not include a measurement error caused by the parasitic resistance.

2. The circuit configuration according to claim 1, wherein the signal-processor unit includes:
   a measurement unit configured to measure the frequency of the oscillator signal;
   a correction-value memory including correction values to compensate for the influence of the parasitic resistance on the frequency of the oscillator signal as a function of the difference between the first measurement of the frequency of the oscillator signal in the first frequency range and the second measurement of the frequency of the oscillator signal in the second frequency range;
   an evaluation unit configured to process a result of at least one of (a) the first measurement and (b) the second measurement with a correction value from the correction-value memory to form a humidity value; and
   a control unit configured to control the measurement processes.

3. The circuit configuration according to claim 1, wherein the switchable impedance includes a reference capacitor and a switch device, and the oscillator is switchable to the second frequency range by a parallel connection of the reference capacitor to the frequency-determining impedance by energizing the switch element.

4. The circuit configuration according to claim 3, wherein the switch element energizable by a control unit of the signal-processor device via a switch line.

5. The circuit configuration according to claim 1, wherein the signal-processor unit is arranged as at least one of (a) an FPGA, (b) an ASIC and (c) a microcontroller.

6. A circuit configuration for measuring air humidity, comprising:
   measuring means including an oscillator unit and signal-processing means, the oscillator unit including oscillating means and switchable impedance means; and
   frequency-determining impedance means including capacitive humidity sensing means and a parasitic resistance means connected in parallel, the frequency-determining impedance means connected to the oscillator unit;
   wherein an oscillation frequency of the oscillating means is a function of (a) the frequency-determining impedance means and (b) a falsifying influence of the parasitic resistance means, the oscillating means switchable from a first frequency range to a second frequency range by connecting the switchable impedance means to the frequency-determining impedance means;
   wherein the oscillator unit is for supplying an oscillator signal having the oscillation frequency of the oscillating means to the signal-processing means, the signal-processing means for measuring the frequency of the oscillator signal and for ascertaining a correction value to compensate for influence of the parasitic resistance means on the oscillation frequency as a function of a difference between a first measurement of the frequency of the oscillator signal in the first frequency range and a second measurement of the frequency of the oscillator signal in the second frequency range;

wherein the influence of the parasitic resistance means on the oscillation frequency of the oscillating means is different in the first frequency range and the second frequency range; and wherein the signal-processing means determines a corrected frequency of the oscillator signal and ascertains a corrected humidity value from the corrected frequency of the oscillator signal that does not include a measurement error caused by the parasitic resistance means.

7. A method for measuring air humidity, comprising:

performing, in a signal-processor unit, a first measurement of a frequency of an oscillator signal in a first frequency range of an oscillator;

switching the oscillator from the first frequency range to a second frequency range by connecting a switchable impedance to a frequency-determining impedance;

performing, in the signal-processor unit, a second measurement of the frequency of the oscillator signal in the second frequency range of the oscillator; and ascertaining a correction value to compensate for an influence of a parasitic resistance on the frequency of the oscillator signal as a function of a difference between the first measurement and the second measurement, the influence of the parasitic resistance on the frequency of the oscillator signal being different in the first frequency range and the second frequency range;

determining a corrected frequency of the oscillator signal based on the correction value; and ascertaining a corrected humidity value from the corrected frequency of the oscillator signal that does not include a measurement error caused by the parasitic resistance.

8. The method according to claim 7, wherein the frequency of the oscillator signal is measured in the signal-processing unit by a measuring unit, the method further comprising outputting a result of the measurements to an evaluation unit.

9. The method according to claim 8, further comprising determining the difference between the first measurement and the second measurement by the evaluation unit;

wherein the evaluation unit ascertains the correction value in the ascertaining step by fetching the correction value from a correction-value memory as a function of the difference between the first measurement and the second measurement.

10. The method according to claim 7, wherein the measurements are controlled by a control unit of the signal-processor unit.

11. The method according to claim 7, wherein the switchable impedance includes a reference capacitor and a switch device, and the oscillator is switched in the switching step to the second frequency range by energizing the switch device by the control unit of the signal-processor unit via a switching line.

12. The method according to claim 11, wherein the energizing of the switch device connects, in parallel, the reference capacitor and the frequency-determining impedance.

13. The method according to claim 7, further comprising processing at least one of (a) a result of the first measurement and (b) a result of the second measurement with the ascertained correction value to form a humidity value.

14. The method according to claim 7, further comprising generating a warning signal if the influence of the parasitic resistance on the frequency of the oscillator signal exceeds a limiting value.

15. The method according to claim 7, wherein the method is performed by the circuit configuration according to claim 1.

16. A method for measuring air humidity, comprising:

performing a first measurement of a frequency of an oscillator signal in a first frequency range of an oscillator;

switching the oscillator from the first frequency range to a second frequency range by connecting a switchable impedance to a frequency-determining impedance;

performing a second measurement of the frequency of the oscillator signal in the second frequency range of the oscillator; and ascertaining a correction value to compensate for an influence of a parasitic resistance on the frequency of the oscillator signal as a function of a difference between the first measurement and the second measurement, the influence of the parasitic resistance on the frequency of the oscillator signal being different in the first frequency range and the second frequency range;

determining a corrected frequency of the oscillator signal based on the correction value; and ascertaining a corrected humidity value from the corrected frequency of the oscillator signal that does not include a measurement error caused by the parasitic resistance.

* * * * *